US00PP28249P3

(12) United States Plant Patent
Bradford et al.

(10) Patent No.: US PP28,249 P3
(45) Date of Patent: Aug. 8, 2017

(54) PEACH TREE NAMED 'PEARL PRINCESS IX'

(50) Latin Name: *Prunus persica*
Varietal Denomination: Pearl Princess IX

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 93 days.

(21) Appl. No.: 14/757,244

(22) Filed: Dec. 11, 2015

(65) Prior Publication Data

US 2017/0172032 P1 Jun. 15, 2017

(51) Int. Cl.
*A01H 5/08* (2006.01)

(52) U.S. Cl.
USPC ..... Plt./196

(58) Field of Classification Search
USPC ..... Plt./196
See application file for complete search history.

(56) References Cited

U.S. PATENT DOCUMENTS

| | | | |
|---|---|---|---|
| PP12,570 | P2 | 4/2002 | Bradford |
| PP15,845 | P2 | 7/2005 | Bradford |
| PP24,700 | P3 | 7/2014 | Bradford |

*Primary Examiner* — Anne Grunberg

(57) ABSTRACT

The present invention relates to a new and distinct variety of peach tree, *Prunus persica*, broadly characterized by a medium size, vigorous, hardy, self-fertile, productive and regular bearing tree. The variety blooms during the early to mid blooming season and requires about 400 chilling hours. The fruit matures under the ecological conditions described in early to mid July with the first picking on Jul. 1, 2015. The fruit is uniform, large in size, globose in shape, freestone in type, firm in texture, white in flesh color, mostly red to pink in skin color, and a tasty balance of light acid and sugar in flavor.

1 Drawing Sheet

Botanical classification: *Prunus persica.*
Variety denomination: 'PEARL PRINCESS IX'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'Pearl Princess IX'.

The present variety was hybridized by us in 2000 as a first generation cross using 'Snow Princess' (U.S. Plant Pat. No. 12,570) peach as the selected seed parent and 'Rose Bright' (U.S. Plant Pat. No. 15,845) nectarine as the selected pollen parent. Upon reaching maturity the fruit from this cross was harvested, and the seeds were removed, cracked, stratified, germinated, and grown as seedlings on their own root in our greenhouse. Upon reaching dormancy the seedlings were transplanted as a group to a cultivated area of our experimental orchard located near Le Grand, Calif., in Merced County (San Joaquin Valley). During the fruit evaluation season of 2005 we selected the present variety as a single tree from the group of seedlings described above. Subsequent to origination of the present variety of peach tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Snow Princess' peach (U.S. Plant Pat. No. 12,570), by having a vigorous tree with large blossoms, by being self-fertile, and by producing freestone peaches that are mostly red to pink in skin color, white in flesh color, globose in shape, and firm in texture, but is distinguished therefrom by having globose instead of reniform leaf glands and by producing fruit that is mildly acidic instead of sub-acidic in flavor and that matures about fourteen days earlier.

The present variety is similar to its pollen parent, 'Rose Bright' nectarine (U.S. Plant Pat. No. 15,845), by having a vigorous tree, by having large blossoms, and by being self-fertile, but is quite distinguished therefrom by producing fruit that is white instead of yellow in flesh color, that is sweeter and less acidic in flavor, that is peach instead of nectarine, and that matures about fifty days later.

The present variety is most similar to 'Ice Queen' peach (U.S. Plant Pat. No. 24,700) by having a vigorous tree, by having large blossoms, by being self-fertile, and by producing white flesh freestone peaches that are mostly red in skin color, globose in shape, and firm in texture, but is distinguished therefrom by having globose instead of reniform leaf glands, by requiring less chilling hours, and by producing fruit that is larger in size and that ripens about seven days earlier.

SUMMARY OF VARIETY

In summary, the present peach variety is characterized by a medium size, vigorous, hardy, self-fertile, productive and regular bearing tree. The variety blooms during the early to mid blooming season and requires about 400 chilling hours. The fruit matures under the ecological conditions described in early to mid July with the first picking on Jul. 1, 2015. The fruit is uniform, large in size, globose in shape, freestone in type, firm in texture, white in flesh color, mostly red to pink in skin color, and a tasty balance of light acid and sugar in flavor.

DRAWING

The accompanying photograph consists of four whole fruits positioned to display the characteristics of the skin color and form, one divided fruit to reveal the flesh and stone, a tip shoot of new leaf growth, typical leaves, and two insets depicting the flower buds and blossoms as they appeared on the tree during the blooming season.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of shipping ripe on Jul. 2, 2015, on a multiplied tree utilizing 'Nemaguard' (unpatented) rootstock during its seventh growing season. The blossom and flower descriptions were made the previous blooming season. All major color code designations are by reference to the Inter-Society Color Council, National Bureau of Standards. Common color names are also used occasionally.

It is to be noted that the 2015 fruit season in California was very warm during the spring and the ripening times of almost all varieties were about twenty days earlier than other years.

PARENTAGE

Seed parent: 'Snow Princess' (U.S. Plant Pat. No. 12,570) peach.

Pollen parent: 'Rose Bright' (U.S. Plant Pat. No. 15,845) nectarine.

TREE

Size: Medium, reaching and maintaining a height of 9' [2.74 m.] and a spread of 8' [2.44 m.] after seven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and moderately dense.

Form: Vase type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 400 hours.

Trunk:

*Size.*—Medium, reaching a maximum diameter of 4½" [114.3 mm.] after the seventh growing season.

*Texture.*—Moderately shaggy.

*Bark color.*—A Moderate brown [58. m.Br] and Grayish brown [61. gy.Br] variegation with Dark brown [59. d.Br] crevices present.

*Lenticels.*—Approximate Number Per Square Inch: 6. Color: Light grayish brown [60. l.gy.Br]. Average Size: ¼" [6.4 mm.] in length. The width is typically one fourth as much as the length. Shape: Eye-shaped.

Branches:

*Size.*—Stocky to medium, diameter of main scaffold is 2⅝" [67 mm.] measured 12" above the crotch, diameter of limb is 1⅞" [48 mm.] measured 12" above the first fork.

*Texture.*—Fairly smooth on first and second year wood, increasing roughness with age.

*Color.*—1st Year Wood Topside: Grayish red [19. gy.R]. 1st Year Wood Underside: Brilliant yellow green [116. brill.YG]. Older Wood: A Deep brown [56. deep Br] and Moderate brown [58. m.Br] variegation.

*Lenticels.*—Number Per Square Inch: About 30 on second year wood. Color: Light yellowish brown [76. l.yBr]. Average Size: Small, 1/64" [0.4 mm.] in length. The width is typically one fourth as much as the length. Shape: Eye-shaped.

Leaves:

*Size.*—Medium to large. Average Length: 5¾" [146.1 mm.]. Average Width: 1½" [38.1 mm.].

*Arrangement.*—Alternate.

*Thickness.*—Medium.

*Form.*—Elliptical.

*Apex.*—Acuminate.

*Base.*—Acute to rounded.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Pale greenish yellow [104. p.gY].

*Petiole.*—Average Length: ½" [12.7 mm.]. Average Thickness: 1/16" [1.6 mm.]. Color: Strong yellow green [117. s.YG].

*Stipules.*—Number: Usually 2 per leaf, up to 6 per growing tip. Average Length: ¼" [6.4 mm.]. Color: Moderate yellow green [120. m.YG] becoming Greyish reddish brown [46. gy.rBr] with age.

*Glands.*—Number: 2 to 6 per leaf. Position: Mostly alternate positioned near the intersection of petiole and base of blade. Form: Globose. Size: Medium, about 1/48" [0.5 mm.] in diameter. Color: Brilliant yellow green [116. brill.YG] acquiring a Moderate reddish brown [43. m.rBr] center with age.

*Leaf buds.*—Pointed, medium in size.

Flower buds:

*Hardiness.*—Hardy, with respect to central California blooming season.

*Diameter.*—Typically ⅜" [9.5 mm.] 1 week before bloom.

*Length.*—Typically ⅝" [15.9 mm.] 1 week before bloom.

*Form.*—Not appressed.
*Surface.*—Pubescent.
*Tip color.*—Light pink [4. l.Pk].

Flowers: Perfect, complete, perigynous, usually a single pistil, about thirty stamens, five sepal and petal locations alternately positioned.
*Type.*—Showy, large.
*Average flower diameter.*—1⅞" [47.6 mm.].
*Average flower depth.*—7/16" [11.1 mm.] when fully open.
*Number of petals.*—Usually five, extra petal fragments occur frequently, double blossoms rarely observed.
*Petal shape.*—Circular to oval.
*Petal margin.*—Entire, wavy.
*Average petal diameter.*—⅝" [15.9 mm.].
*Average petal length.*—11/16" [17.5 mm.].
*Petal apex.*—Rounded.
*Petal base.*—Rounded to somewhat truncate.
*Petal color.*—Light pink [4. l.Pk] toward the apex, Deep pink [3. deep Pk] toward the base on both sides.
*Anther color.*—Moderate red [15. m.R] over a Light yellow [86. l.Y] center at bloom onset.
*Pollen.*—Anthers produce an abundance of Brilliant yellow [83. brill.Y] pollen.
*Stigma color.*—Light greenish yellow [101. l.gY].
*Stigma position.*—Typically located about 1/16" [1.6 mm.] below the nearby anthers.
*Average pistil length.*—⅝" [15.9 mm.].
*Average stamen length.*—9/16" [14.3 mm.].
*Ovary.*—Pubescent.
*Sepal color.*—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.
*Sepal length.*—¼" [6.4 mm.].
*Sepal width.*—3/16" [4.8 mm.].
*Sepal apex.*—Rounded to elliptical to match the sepal length and width.
*Sepal margin.*—Fairly smooth.
*Fragrance.*—Moderate.
*Blooming period.*—Medium to early, four days before 'Snow Princess' (U.S. Plant Pat. No. 12,570) peach.
*Onset of bloom.*—One percent on Feb. 12, 2015.
*Date of full bloom.*—Feb. 22, 2015.
*Duration of bloom.*—One to two weeks, dependent on ambient temperature.
*Bloom density.*—Medium to heavy.
*Number per cluster.*—1 to 3 with single flowers most common.

FRUIT

Maturity when described: Shipping ripe, Jul. 2, 2015.
Date of first picking: Jul. 1, 2015.
Date of last picking: Jul. 10, 2015.
Size: Uniform, large.
*Average diameter axially.*—3 7/16" [87.3 mm.].
*Average diameter across suture plane.*—3¼" [82.6 mm.].
*Average diameter across cheek plane.*—3⅜" [85.7 mm.].
*Typical weight.*—11.1 ounces [315 grams].
Form: Uniform, globose, mostly symmetrical.
*Longitudinal section form.*—Round.
*Axial view.*—Round.
Suture: A shallow groove that extends from the base, continues along the side, and ends just beyond the pistil point.
*Near the base.*—A sharp groove.
*Along the side.*—A shallow trough.
*Near the apex.*—A shallow groove.
Ventral surface: Rounded slightly, lipped toward the apex on both sides.
Lips: Fairly equal.
Cavity: Flaring, elongated in the suture plane, Pale greenish yellow [104. p.gY] stem markings typical.
*Depth.*—½" [12.7 mm.].
*Breadth.*—1½" [38.1 mm.].
Base: Truncate, slightly cordate if viewed parallel to the suture.
Apex: Rounded with a slight mammiform protrusion.
Pistil point: Oblique, an inconspicuous Dark grayish brown [62. d.gy.Br] dot.
Stem: Medium.
*Average length.*—7/16" [11.1 mm.].
*Average width.*—⅛" [3.2 mm.].
Skin:
*Thickness.*—Medium.
*Surface.*—Pubescent.
*Tenacity.*—Tenacious to flesh.
*Astringency.*—Non-astringent.
*Tendency to crack.*—None observed.
*Color.*—A Dark red [16. d.R] over a Light yellowish pink [28. l.yPk] background with some Pale greenish yellow [104. p.gY] areas where sun protected.
*Down.*—Short, does not roll up when rubbed.
Flesh:
*Color.*—Greenish white [153. gWhite] with Deep red [13. deep R] streaking toward stone.
*Surface of pit cavity.*—Covered with Very red [11. v.R] fibers.
*Amygdalin.*—Mild.
*Juice.*—Moderate, rich.
*Texture.*—Firm, crisp.
*Fibers.*—Abundant toward the pit.
*Ripens.*—Fairly evenly.
*Flavor.*—A tasty balance of acid and sugar, typically 17 brix.
*Aroma.*—Moderate.
*Eating quality.*—Very good.

STONE

Type: Freestone.
Form: Oval.
Hilum: Narrow.
Base: Rounded.
Apex: Rounded with a ⅛" [3.2 mm.] tip.
Sides: Unequal.
Surface: Irregularly furrowed toward the apex, pitted toward the base.
Ridges: Jagged.
External color: Very deep red [14. v.deep R] when first removed, Grayish reddish brown [46. gy.rBr] when dry.
Pit wall color when cracked: Light grayish yellowish brown [79. l.gy.yBr].
Cavity surface color: Deep yellowish brown [75. deep yBr].
Average pit wall thickness: ¼" [6.4 mm.].
Average length: 1 9/16" [39.7 mm.].

Average width: 1" [25.4 mm.].
Average breadth: 15/16" [23.8 mm.].
Tendency to split: None observed.
Kernel:

*Form.*—Oval.
*Skin color.*—Pale yellow [89. p.Y].
*Pellicle color.*—Dark yellowish brown [78. d.yBr].
*Vein color.*—Brilliant yellow [83. brill.Y].
*Taste.*—Bitter.
*Viable.*—Yes.
*Average width.*—1/2" [12.7 mm.].
*Average length.*—3/4" [19.1 mm.].
*Amygdalin.*—Moderate.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to 'Ice Queen' peach (U.S. Plant Pat. No. 24,700) by having a vigorous tree, by having large blossoms, by being self-fertile, and by producing white flesh freestone peaches that are mostly red in skin color, globose in shape, and firm in texture, but is distinguished therefrom by having globose instead of reniform leaf glands, by requiring less chilling hours, and by producing fruit that is larger in size and that ripens about seven days earlier.

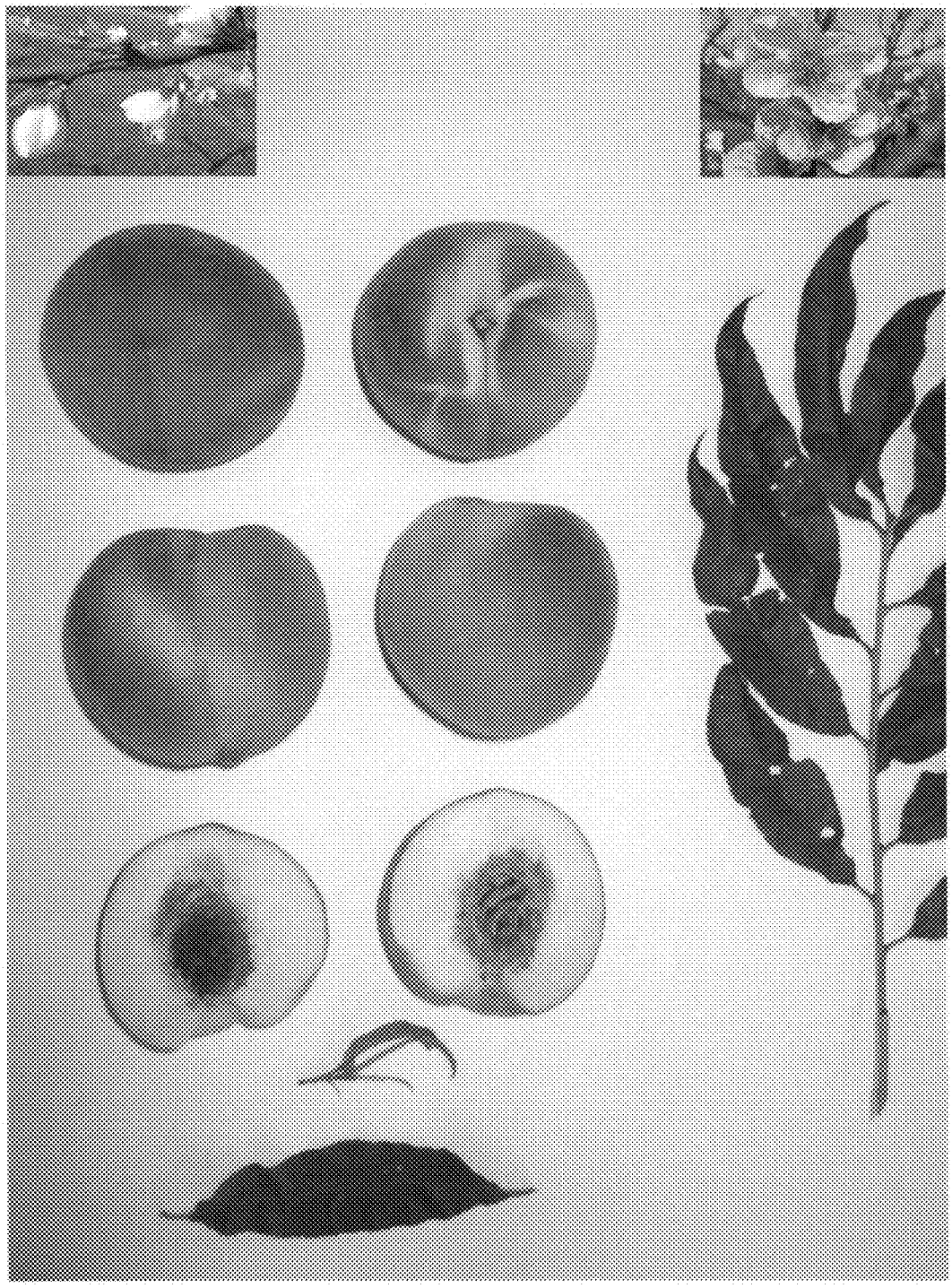

* * * * *